US006682631B2

(12) United States Patent
Cole

(10) Patent No.: US 6,682,631 B2
(45) Date of Patent: *Jan. 27, 2004

(54) EVAPORATOR AND EVAPORATION PROCESS

(75) Inventor: Michael Cole, Molesford (GB)

(73) Assignee: Genevac Limited, Ipswich (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 153 days.

(21) Appl. No.: 09/341,718
(22) PCT Filed: Dec. 8, 1998
(86) PCT No.: PCT/GB98/03661
§ 371 (c)(1),
(2), (4) Date: Jul. 15, 1999
(87) PCT Pub. No.: WO99/33538
PCT Pub. Date: Jul. 8, 1999

(65) Prior Publication Data
US 2002/0029953 A1 Mar. 14, 2002

(30) Foreign Application Priority Data
Dec. 23, 1997 (GB) ................................. 9727232

(51) Int. Cl.$^7$ ............... B01D 3/08; B01D 3/10; B01D 3/42; B04B 9/10
(52) U.S. Cl. ............ 159/6.1; 159/44; 159/47.1; 159/DIG. 16; 210/512.1; 494/7; 494/16; 494/61; 494/84
(58) Field of Search ............... 159/44, 6.1, DIG. 16, 159/DIG. 26, DIG. 42, 47.1; 219/10.55; 202/238, 160, 205, 265, 175; 333/230; 318/3; 494/16, 7, 61, 84; 210/512.1, 97, 138; 422/101

(56) References Cited

U.S. PATENT DOCUMENTS

| 3,304,990 | A | | 2/1967 | Ontko ........................... 159/6 |
| 4,226,669 | A | | 10/1980 | Vilardi ....................... 159/6 R |
| 4,403,939 | A | | 9/1983 | Rothschild ................. 425/425 |
| 4,857,811 | A | | 8/1989 | Barrett ........................... 318/3 |
| 5,137,604 | A | * | 8/1992 | Meeks et al. .............. 202/205 |
| 5,211,808 | A | * | 5/1993 | Vilardi et al. ............... 159/6.1 |
| 5,217,572 | A | * | 6/1993 | Guy et al. ................. 159/16.1 |
| 5,334,130 | A | * | 8/1994 | Glater et al. .................. 494/4 |
| 5,415,616 | A | | 5/1995 | Wright ........................ 494/16 |
| 5,431,620 | A | | 7/1995 | Schenck ....................... 494/7 |
| 5,464,531 | A | * | 11/1995 | Greene ...................... 392/325 |

FOREIGN PATENT DOCUMENTS

| DE | 41 13 174 | 1/1992 |
| EP | 0 592 354 | 4/1994 |
| GB | 2 230 203 | 10/1990 |
| GB | 2 246 192 | 1/1992 |
| SU | 1754139 | 8/1992 |

OTHER PUBLICATIONS

"Eppendorf Vacufuge (RTM) Concentrator," 1997.
Genevac Limited, "All About Bumping".

* cited by examiner

Primary Examiner—Virginia Manoharan
(74) Attorney, Agent, or Firm—Barnes & Thornburg

(57) ABSTRACT

A centrifugal evaporator for evaporating a mixture of liquids having different volabilities and specific gravities, the mixture being contained in a test tube 14 pivotally mounted on a rotatable support arm 12 in a sealable vacuum chamber 16, the support arm is rotated up to a speed of the order of 2000 rpm before evaporation of the more volatile component occurs, and only then is the chamber progressively evacuated. The motor is preferably a three-phase induction motor connected to the electric supply in a frequency convertor.

9 Claims, 3 Drawing Sheets

Fig. 1a — *Prior Art*

EVAPORATOR AND EVAPORATION PROCESS

FIELD OF INVENTION

This invention concerns centrifuged evaporators and processes for evaporation primarily but not exclusively for separating volatile components from less volatile components of liquid mixtures typically but not exclusively volatile solvents and solvent components in liquid mixtures.

BACKGROUND TO THE INVENTION

In the preparation of pharmaceuticals and drugs it is a common requirement to separate an unwanted volatile solvent component from less volatile materials and one technique which has been developed involves centrifuging the mixture while simultaneously evacuating the chamber containing the centrifuge material so as to draw off from the mixture the more volatile component and leave the less volatile material behind. Thus chemists and biologists frequently need to remove liquids in which the solid matter in which they are interested is dissolved or suspended. The solid matter may be potential new drugs, biological samples or other materials. They are frequently sensitive to heat, so that the liquid cannot be boiled off at atmospheric pressure because this would involve excessively high temperatures. Boiling, or evaporation under vacuum is often the preferred process because this can be done at low temperatures which do not harm the samples. If samples in liquids are exposed to vacuum the tend to boil vigorously and this activity can lead to liquid containing valuable sample material being spilled and lost, or worse, to cross-contamination of samples which may have just been expensively purified.

It is therefore well known to spin such samples in a closed vacuum chamber so as to subject them to rotation generated centrifugal forces which suppress the spitting or frothing of the liquid while it is boiling under vacuum. This process is known as Centrifugal Evaporation, or Concentration.

A typical arrangement comprises a stationary chamber which can be sealed and evacuated and within which is mounted a rotatable support carrying a number of test tube like containers which are gimbled at their upper ends and which will normally hang vertically when the support is stationary but will swing upwardly and assume a more horizontal attitude as the support is rotated at high speed.

Whilst the chamber is at atmospheric pressure and either contains air or gas at atmospheric pressure, the resistance to motion as the test tube devices are rotated increases particularly as the test tube devices rotate into their more horizontal attitude. This limits the speed of rotation and typically the power units associated with conventional centrifuges have been sufficient to attain a rotational speed of approximately 1,000 RPM whilst the chamber is at or near atmospheric pressure. However as the chamber is evacuated the resistance to rotation decreases and the rotational speed can rise. Thus current practice is to spin the samples as fast as can be achieved, with conventional drive motors at atmospheric pressure, before evacuating the chamber. This is typically about 1000 RPM which might provide a centrifugal force of around 150 g. The chamber is then evacuated and the rotor spins faster as the pressure drops due to the reduction in drag caused by the residual air in the chamber, and most equipment in use achieves a final rotor speed in the range 1350–1750 RPM at vacuum.

After the process is completed, the chamber is repressurised to atmospheric pressure and the motor is run down, and as the apparatus becomes stationary the gimbled test tube devices rotate into their vertical mode and can be removed.

Whilst apparatus and a method of operation such as described has proved satisfactory for some solvent containing mixtures, a problem has arisen where such apparatus and method has been used to remove two solvent components from such a mixture, where the solvent components have different volatilities and different specific gravities. In this case unpredictable behaviour has been observed coupled with spitting and uncontrolled emission of one or both of the components, which can cause contamination if it enters some of the other test tube devices instead of being systematically and cleanly evacuated from the chamber. In particular, the known process is not appropriate for mixtures of liquids consisting of a dense volatile liquid such as dichloromethane (DCM), or chloroform, mixed with less dense and less volatile liquids such as methanol. It is found that severe spitting leading to sample loss and cross-contamination can occur with such liquid mixtures, under the same conditions in which neither liquid will spit if processed alone.

This can even occur where the mixture of the liquids is homogeneous and the solvents are fully miscible so that no segregation occurs under the action of centrifugal force. However as soon as a partial vacuum is applied, preferential evaporation of the more volatile component takes place from the surface of the mixed liquid, leaving the top layer depleted in that liquid and therefore less dense and less volatile than the bulk liquid below. It therefore forms a non-evaporating liquid blanket, which prevents the bulk liquid evaporating. If the pressure in the chamber is then lowered further the bulk liquid becomes superheated because, although its temperature may not change, the lowered pressure has the effect of raising the temperature of the liquid above its boiling temperature. This causes it to boil very vigorously as nuclei are formed. This boiling bulk liquid penetrates the liquid blanket and leaves the container, causing sample loss and the possibility of cross-contamination.

It is an object of the present invention to provide an improved apparatus and method for centrifugal evaporation of solvent mixtures so as to obviate the identified problem.

SUMMARY OF THE INVENTION

According to one aspect of the present invention there is provided a method of evaporating a mixture of liquids having different volatilities and different specific gravities from a mixture in a container of such liquids and other non-volatile materials, comprising the steps of centrifuging the mixture whilst still under a positive pressure, as opposed to a vacuum, at a sufficiently high speed of rotation before evaporation of the more volatile component occurs, and only thereafter progressively evacuating a sealable chamber enclosing the container, so as to reduce the pressure and cause the volatile components to evaporate under the reduced pressure conditions.

The chamber may be returned to normal pressure after the volatile components have been evaporated and collated, after which the rotating device is run down to allow the material left in the containers to be collected.

The invention constrains the different components of the mixture and ensures a more controlled evaporation than would occur at lower rotation-generated centrifugal forces.

Existing apparatus is not capable of performing this method since the motor power hitherto provided in evaporating centrifuges has been insufficient to spin the material to be centrifuged at a sufficiently high speed in a gaseous environment in which the gas pressure is sufficiently high to prevent evaporation of the more volatile component before the pressure is reduced.

According to another aspect of the present invention, apparatus for performing the above method comprises a sealable chamber and vacuum pump associated therewith to enable the chamber to be evacuated, a motor for rotating a support within the chamber, at least one container mounted on the support for containing a mixture of materials having differing volatilities and specific gravities, and a control system for controlling the operation of the apparatus, wherein the power of the motor is sufficient to rotate the support and the container at a sufficiently high speed before the pressure in the chamber is lowered below that at which the more volatile component will evaporate to prevent unwanted agitated boiling of more dense volatile components from the mixture.

In practice the motor will in general need to provide sufficient torque to be able to rotate the assembly faster, at a moderate positive pressure of say ½ atmosphere, than it is required to rotate the assembly at full vacuum.

Sensors may be provided for indicating to the control system the pressure within the chamber, the rotational speed of the support within the chamber, the solvent content of the gases in or leaving the chamber during the evacuation thereof, and the temperature of the liquid mixture in the container.

Programmable means may be provided for supplying power to the motor to rotate the support and the container, and for operating the vacuum pump to the chamber only after the speed sensor indicates that a sufficient rotational speed has been achieved.

Means may be provided for removing the vacuum as by slowly shutting down the vacuum pump or slowly by-passing the latter to allow the pressure within the chamber to slowly revert to atmospheric pressure, and to remove power from the motor in a controlled manner to allow the assembly to run down, and if provided, to apply controlled braking to the rotatable support to reduce its rotational speed, albeit in a controlled manner.

An interlock is preferably provided such that centrifuging and evacuation cannot be performed unless the chamber has been closed and sealed.

The process may be automated by means of a process timer or by using information derived from a sensor in the feed to the vacuum pump such that the evacuation process is only terminated after a predetermined low level of solvent concentration in the gaseous mixture, has been attained.

The containers containing the materials which are to be centrifuged may be in the form of test tubes which are gimbled near their open upper end to the support by which they can be rotated, and which normally hang in a generally vertical manner but with rotation assume a generally horizontal mode with the closed end of each tube outermost, the liquid in the tube being constrained to remain at the closed end of the tube due to the forces generated by the rotation.

Alternatively each rotatable container may comprise a chamber containing a well for the liquid contents and an inclined surface leading from the lower region of the well to a radially outwardly displaced elevated region of the chamber up and along which the liquid contents flow so as to enter the elevated region under the forces generated during rotation, and from which region the liquid mixture will flow down to return to to the well as the rotational speed drops, and the forces due to rotation diminish.

Such alternative chambers obviate the need for gimballed test-tube like devices.

BRIEF DESCRIPTION OF THE DRAWINGS

The invention will now be described, by way of example, with reference to the accompanying drawings in which FIG. 1a shows a known evaporator when stationary.

DESCRIPTION OF THE PREFERRED EMBODIMENT

Figure 1B:
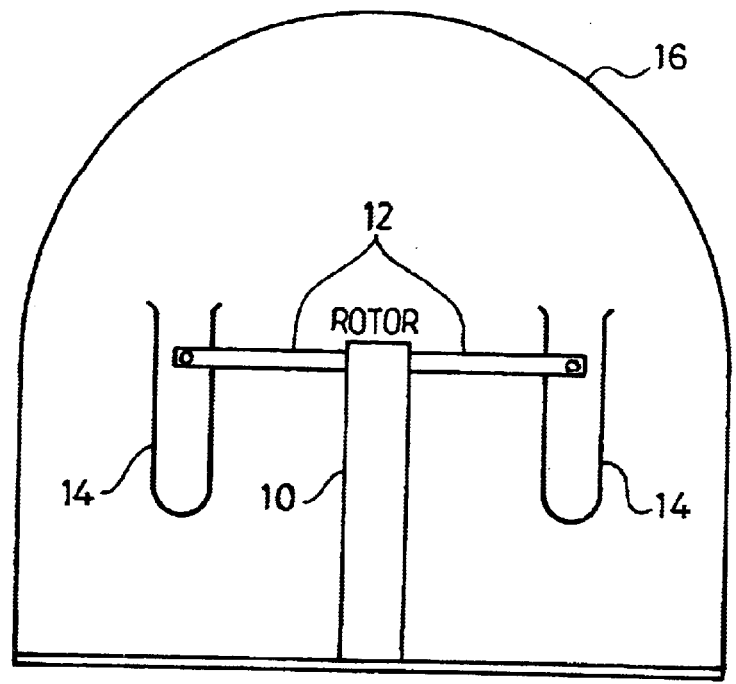
FIG. 1b shows the same evaporator when rotating, but modified in accordance with the invention.
Figure 1B:
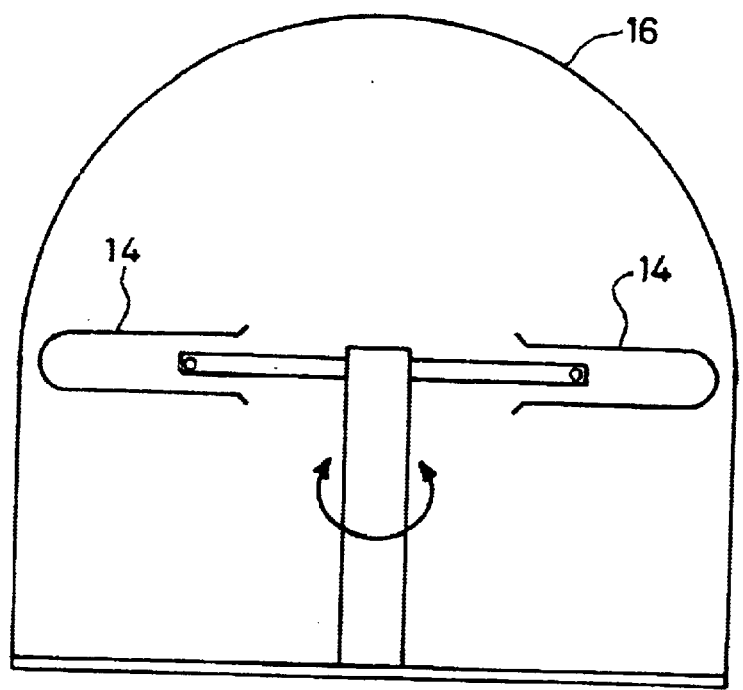

The centrifuge comprises a rotor 10 driven by a motor 11 via a power supply 13 carrying several support arms 12, of which only two are shown. Gimballed or pivotally mounted about the end of each arm is a test tube 14 for containing a homogenous mixture of a sample or the like dissolved in two volatile liquid components. The whole apparatus is contained in a bell shaped vacuum chamber 16 which is connected to a suction pump 15, enabling the chamber to be at least partially evacuated so that the ambient pressure therein is reduced to a partial vacuum, as measured by a pressure sensor 17.

The presence of the two volatile liquid components in the test tubes 14 can cause uneven boiling and spitting as described above, and this is illustrated in FIGS. 2a to 2c.

Figure 2A:
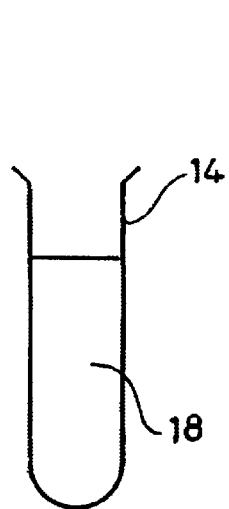
FIGS. 2(a)–2(c) illustrate a test tube containing a mixed liquid in three conditions of evaporation.

FIG. 2a illustrates a tube 14 containing such a homogeneous mixed liquid 18.

Figure 2B:
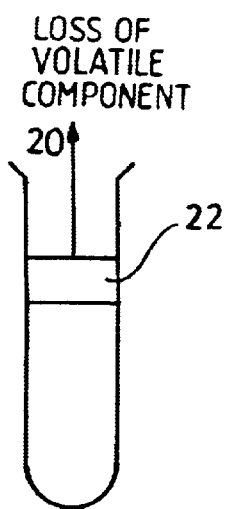

FIG. 2b shows the same tube after exposure to a partial vacuum. Due to the loss of the more volatile liquid component 20, a surface layer 22 has formed, typically a few millimeters thick, of a liquid containing less of the heavier, more volatile component.

Figure 2C:
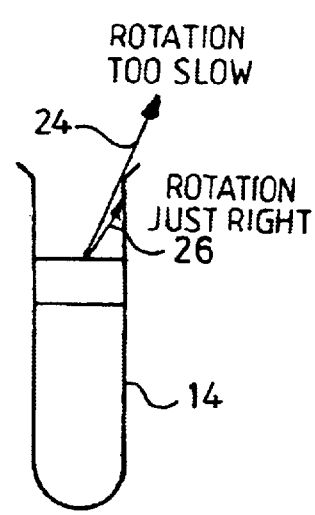

FIG. 2c illustrates the explosive spitting which occurs when the pressure is reduced to a value at which the bulk liquid is superheated, ie its temperature is above its boiling point at that pressure.

When spitting occurs the ejected liquid is propelled towards the centre of rotation and is not affected by the rotation from the instant that it leaves the liquid surface 22. The tube containing the sample is rotating and the path of the spitting liquid emerging from the liquid surface is inclined to the axis of the tube at an angle depending on the relative velocities of the spitting liquid and the tube. If the rotation of the tube is too slow, the spitting liquid will escape, as shown by the arrow 24. But if, in accordance with the invention, rotation is fast enough, the spitting liquid will hit the wall of the tube and be thrown back towards the bottom of the tube by the centrifugal force, as shown by arrow 26.

Thus, in accordance with the invention, it has been found that spitting from these mixed liquids can be prevented by procuring sufficiently fast rotation of the tubes before the volatile component of the mixture starts to evaporate. This requires a considerably faster and several times more powerful motor than is normally used in centrifugal evaporators, as described below, because the drag on an assembly of tubes rotating at one half or one third of an atmosphere is much grater than that under vacuum.

The procedure is therefore to ensure, via a speed sensor or controller 32, that the samples are rotating at about 2000 rpm in the evaporator in which the samples are rotated at a radius of 120 cms, to give a centrifugal force of about 450 g. Initial fast pump down then commences, allowing the pressure to fall to that at which evaporation of the most volatile component of the mixture begins to occur at the sample temperature, at which it is held, i.e. a pressure just above that at which the volatile component would boil. Typically this pressure is in the range 350–400 mbar in the case of mixtures containing DCM for sample temperatures around 25° C.

The pressure is next gradually reduced at a controlled rate by a vacuum controller so that gross superheating does not occur. The rate of pressure reduction can be controlled through knowledge of actual sample temperature, by a suitable temperature sensor 36 (eg the SampleGuard by Genevac Ltd), or by experiment. The reduction rate or ramp rate will depend upon the particular liquid component being evaporated, and the lowest safe pressure is normally the full vacuum achievable in the system, although in some cases it may have to be higher.

The reason the pressure can be lowered is that the sample cools as the liquid components evaporate and the cooler it gets, the lower the pressure which can be tolerated in the chamber 16.

The reduced pressure is then maintained until the sample in the tube 14 is dry, at which point the pressure is allowed to rise to atmospheric pressure and the rotor 10 stopped.

Figure 3:
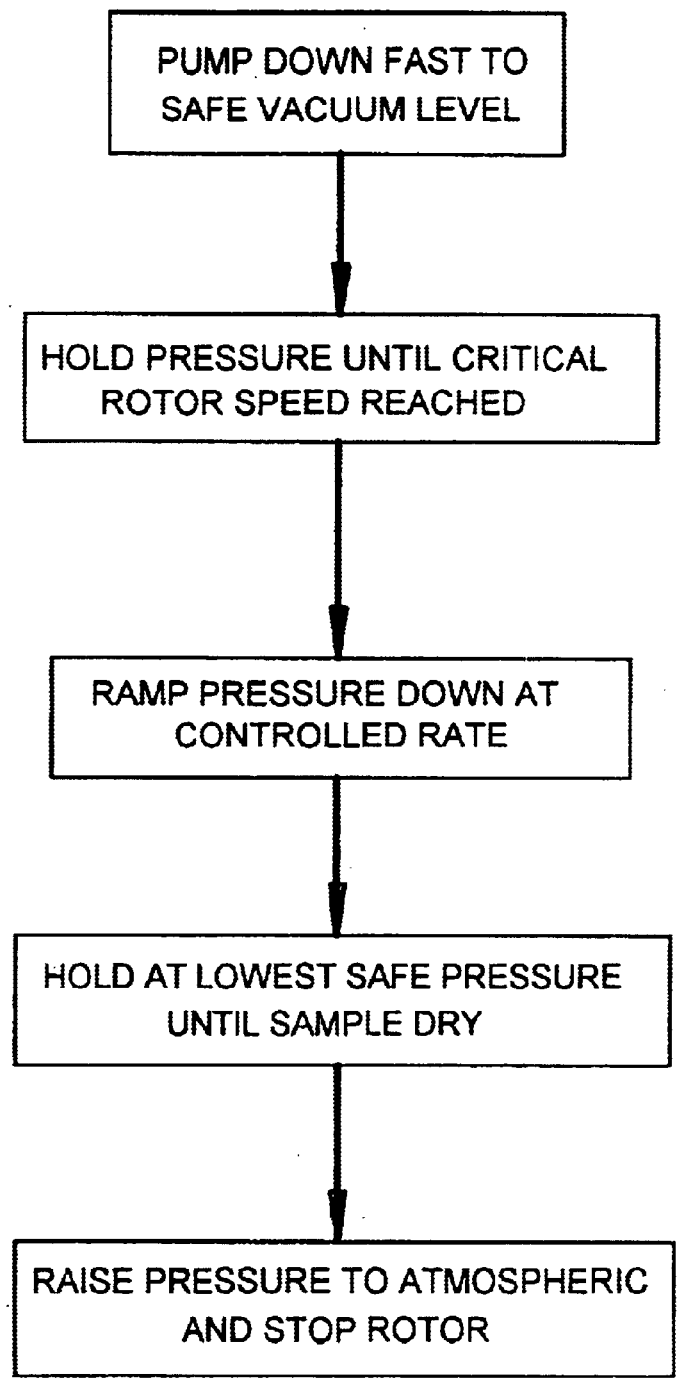
FIG. 3 is a flow chart of an evaporation process for the prevention of splitting the liquid.

The sequence of stages in this procedure is depicted in the flow chart control system shown in FIG. 3.

A suitable electric motor for rotating the rotor 10 at the higher speed of about 2000 rpm referred to above, is a 3-phase supply. This provides a higher torque than a single phase motor for a given physical size.

An alternative would be to use a DC motor with a speed controller. Both these alternatives are more expensive than the smaller single phase induction motors used in conventional centrifugal evaporators, which operate at only about 1400 rpm on 50 Hz supply or 1600 rpm on 60 Hz supply.

What is claimed is:

1. A method of centrifugal evaporation of at least two solvent components having different volatilities and different specific gravities from a mixture of such components and other less volatile materials contained in at least one container and in which the more volatile solvent component has a higher specific gravity than the other less volatile solvent component or components, the at least one container being rotatable about an axis spaced therefrom, comprising the steps of centrifuging the mixture while still under atmospheric pressure, and thereafter progressively evacuating a sealable chamber enclosing the at least one container under the control of a control system, so as to reduce the pressure and cause the volatile components to boil under the reduced pressure conditions, determining the temperature of the mixture by means of a temperature sensor connected to said control system, and before the pressure is reduced below a value at which the more volatile component will boil, rotating the at least one container at a speed sufficiently high so as to generate a centrifugal force of approximately 450 times the gravitational force which gravity exerts on the mixture in the at least one container when at rest, such that any emissions from the surface of the mixture are retained within the confines of the at least one container once boiling occurs.

2. A method according to claim 1 in which said speed of the at least one container is achieved when the pressure within said sealable chamber is ½ atmosphere.

3. Apparatus for centrifugal evaporation of a mixture of at least two solvent components and other less volatile materials in which the more volatile component has a higher specific gravity than the other less volatile solvent component or components of the mixture, comprising a sealable chamber, a vacuum pump associated therewith to enable the chamber to be evacuated, a motor for rotating a support within the chamber, a power supply for energizing the motor, at least one container mounted on the support for rotation about an axis spaced therefrom, and containing said mixture of solvents and materials having differing volatilities and specific gravities, and a control system for controlling the operation of the apparatus, wherein the motor can be supplied with sufficient energy and will generate sufficient torque to rotate the support and the at least one container at a sufficiently high speed to generate a centrifugal force of approximately 450 times the force which gravity exerts on the mixture in the at least one container when at rest, and the control system inhibits the reduction of the pressure in the chamber below that at which the more volatile solvent component will boil until that said sufficiently high speed is attained, thereby to prevent loss from the at least one container of surface emissions caused by agitated boiling in the mixture, and in which the at least one container comprises a chamber containing a well for the liquid contents and an inclined surface leading from the lower region of the well to a radially outwardly displaced elevated region of the chamber up and along which the liquid contents flow so as to enter the elevated region under the forces generated during rotation, and from which region the liquid mixture will flow down to return to the well as the rotational speed drops, and the forces due to rotation diminish.

4. Apparatus according to claim 3 in which the motor provides sufficient torque to rotate the support at the required speed when the pressure within the chamber is ½ atmosphere.

5. Apparatus according to claim 3 in which the motor is a three-phase induction motor connected to an electricity supply via a frequency convertor.

6. Apparatus according to claim 3 in which the motor is a DC motor with a speed controller.

7. Apparatus according to claim 3 in which said at least one container comprises test tubes which are gimbled adjacent their open upper end to the support by which they can be rotated, and which normally hang in a generally vertical manner but with rotation assume a generally horizontal mode with the closed end of each tube outermost, the liquid in the tube being constrained to remain at the closed end of the tube due to the forces generated by the rotation.

8. Apparatus for centrifugal evaporation of a mixture of at least two solvent components having differing volatilities and specific gravities, and other less volatile materials, comprising a sealable chamber, a vacuum pump associated therewith to enable the chamber to be evacuated, a motor for rotating a support within the chamber, a power supply for energizing the motor, at least one container mounted on the support for rotation about an axis spaced therefrom, and containing said mixture of solvents and materials, a control system for controlling the operation of the apparatus, a speed sensor for indicating the rotational speed of the support, a pressure sensor for indicating the pressure within the chamber, and a temperature sensor, said sensors being connected to the control system, wherein the motor can be supplied with sufficient energy and will generate sufficient torque to rotate the support and the at least one container at a sufficiently high speed to generate a centrifugal force of approximately 450 times the force which gravity exerts on the mixture in the container when at rest, and the control system inhibits the reduction of the pressure in the chamber below that at which the more volatile solvent component will boil until said sufficiently high speed is attained, thereby to prevent loss from the at least one container of surface emissions caused by agitated boiling in the mixture, and in which the motor provides sufficient torque to rotate the support, at the required speed when the pressure within the chamber is ½ atmosphere.

9. Apparatus according to claim 8 in which said at least one container for containing the mixture comprises test tubes which are gimbled adjacent their open upper end to the support by which they can be rotated, and which normally hang in a generally vertical manner but with rotation assume a generally horizontal mode with the closed end of each tube outermost, the liquid in the tube being constrained to remain at the closed end of the tube due to the forces generated by the rotation.

* * * * *